United States Patent
Kotani (10) Patent No.: US 7,215,421 B2
(45) Date of Patent: May 8, 2007

(54) FLUORESCENCE LIFETIME MEASUREMENT APPARATUS

(75) Inventor: Tadashi Kotani, Tokyo (JP)

(73) Assignee: Olympus Corporation, Tokyo (JP)

( * ) Notice: Subject to any disclaimer, the term of this patent is extended or adjusted under 35 U.S.C. 154(b) by 448 days.

(21) Appl. No.: 10/912,784

(22) Filed: Aug. 6, 2004

(65) Prior Publication Data

US 2005/0030532 A1  Feb. 10, 2005

(30) Foreign Application Priority Data

Aug. 8, 2003 (JP) ............... 2003-290445
Jul. 30, 2004 (JP) ............... 2004-223466

(51) Int. Cl.
*G01J 3/30* (2006.01)
(52) U.S. Cl. .................. 356/317; 356/318
(58) Field of Classification Search ............ 356/317, 356/318, 417; 250/458.1, 459.1, 461.1
See application file for complete search history.

(56) References Cited

U.S. PATENT DOCUMENTS 5,485,530 A * 1/1996 Lakowicz et al. ......... 382/191
6,809,816 B2 * 10/2004 Sharma ..................... 356/318
2005/0072936 A1 * 4/2005 Kotani ..................... 250/458.1

FOREIGN PATENT DOCUMENTS

GB  2382648  *  6/2003
JP  2002-107300 A  4/2002

OTHER PUBLICATIONS

H.C. Gerritsen et al; Fluorescence Lifetime Imaging in Scanning Microscopes: Acquiisition Speed, Photon Economy and Lifetime Resolution; 2002 The Royal Microscopical Society; vol. 206; Jun. 2002; pp. 218-223.

* cited by examiner

*Primary Examiner*—Layla G. Lauchman
(74) *Attorney, Agent, or Firm*—Frishauf, Holtz, Goodman & Chick, P.C.

(57) ABSTRACT

A fluorescence lifetime measurement apparatus includes a first controller controlling a total gate length and a second controller controlling a start gate length of a plurality of gate lengths into which the total gate length is divided. The start gate length is a time window whose start time is when measurement of the number of fluorescence photons of a specimen starts. The apparatus also includes a measurer measuring the number of fluorescence photons for each of the gate lengths; a processor calculating a fluorescence lifetime the specimen based on the start gate length and the number of fluorescence photons; and a third controller causing, when the fluorescence lifetime does not satisfy a predetermined condition, the first and second controllers to change the start gate length and the total gate length.

11 Claims, 13 Drawing Sheets

MEASURED NUMBER OF FLUORESCENCE PHOTONS

FLUORESCENCE LIFETIME MEASUREMENT APPARATUS

CROSS-REFERENCE TO RELATED APPLICATIONS

This application claims the benefit of priority of Japanese Patent Applications No. 2003-290445 filed on Aug. 8, 2003 and No. 2004-223466 filed on Jul. 30, 2004 the entire contents of which are incorporated herein by reference.

BACKGROUND OF THE INVENTION

1) Field of the Invention

The present invention relates to a fluorescence lifetime measurement apparatus that calculates a fluorescence lifetime by measuring the number of fluorescence photons emitted from a specimen which is irradiated with excitation light.

2) Description of the Related Art

There is known a method of calculating a fluorescence lifetime by irradiating a specimen with excitation light to excite the specimen, and by measuring the number of fluorescence photons emitted from the specimen. In particular, in a field of biochemistry, attention is paid to a fluorescence lifetime measurement apparatus using pulse excitation light because a microstructure of a living body can be clarified by creating a fluorescence lifetime distribution image. As a method of calculating the fluorescence lifetime, there is known a time correlated single photon counting (TCSPC) in which a specimen is irradiated with pulse excitation light and a time until fluorescence photons are received is measured (see Japanese Patent Application Laid-Open No. 2002-107300).

There is also known a time gate method in which (1) a specimen is irradiated with pulse excitation light, (2) the number of fluorescence photons emitted from the specimen in a plurality of time windows each referred to as "a time gate" is measured, and then (3) the fluorescence lifetime is calculated from the number of fluorescence photons measured.

The TCSPC requires that the number of fluorescence photons emitted by the irradiation of one pulse excitation light be a very small number of about 0.01 piece. Accordingly, the specimen must be irradiated with pulse excitation light at least several tens of thousands of times to calculate the fluorescence lifetime once, and thus it takes a very long time to calculate of the fluorescence lifetime.

On the other hand, the time gate method can effectively use pulse excitation light. However, setting a plurality of time gates inappropriately makes a large error in a calculated fluorescence lifetime. Therefore, the time gates must be appropriately set to reduce the error of the fluorescence lifetime. Thus, when a fluorescence lifetime of an unknown specimen is measured in the time gates fixed, if the time gates fixed are inappropriate, it is difficult to reduce the error of the fluorescence lifetime.

SUMMARY OF THE INVENTION

A fluorescence lifetime measurement apparatus according to one aspect of the present invention includes a light source irradiating a specimen with excitation light, a first controller, a second controller, a measurer, a processor, and a third controller. The first controller controls a total gate length that is a total time window during which a number of fluorescence photons emitted from the specimen excited by the excitation light is measured. The second controller controls a start gate length of a plurality of gate lengths into which the total gate length is divided. The start gate length is a time window whose start time is when measurement of the number of fluorescence photons starts. The measurer measures the number of fluorescence photons for each of the gate lengths. The processor calculates a fluorescence lifetime the specimen based on the start gate length and the number of fluorescence photons measured by the measurer. The third controller causes, when the fluorescence lifetime does not satisfy a predetermined condition, the first controller and the second controller to change the start gate length and the total gate length.

The other objects, features, and advantages of the present invention are specifically set forth in or will become apparent from the following detailed description of the invention when read in conjunction with the accompanying drawings.

DETAILED DESCRIPTION

Exemplary embodiments of a fluorescence lifetime measurement apparatus according to the present invention is explained below in detail with reference to the accompanying drawings.

Figure 1:
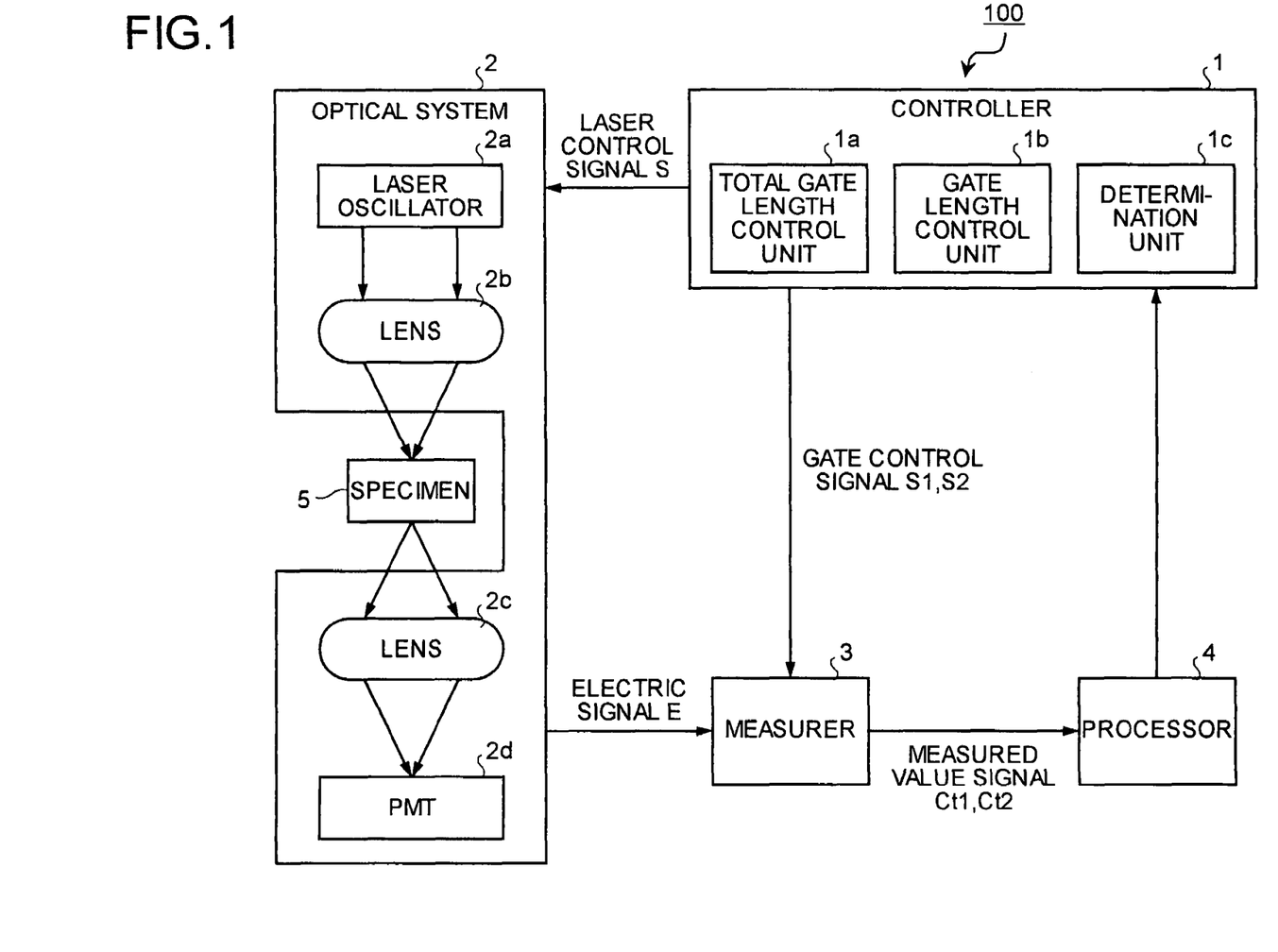
FIG. 1 is a block diagram of a fluorescence lifetime measurement apparatus according to a first embodiment of the present invention.

FIG. 1 is a block diagram of a fluorescence lifetime measurement apparatus 100 according to a first embodiment of the present invention. The fluorescence lifetime measurement apparatus 100 includes a controller 1, an optical system 2, a measurer 3, and a processor 4.

The controller 1 includes a total gate length control unit 1a, a gate length control unit 1b, and a determination unit 1c. The total gate length control unit 1a controls a total gate length that is a total time window from a start to an end of measurement of the number of fluorescence photons. The gate length control unit 1b controls each gate length obtained by dividing the total gate length into a plurality of gate lengths. The determination section 1c determines whether a calculated value of a fluorescence lifetime satisfies a predetermined condition and settles the fluorescence lifetime.

The optical system 2 includes a laser oscillator 2a, lenses 2b and 2c, and a photo multiplier tube (PMT) 2d acting as a photoelectric converter. The laser oscillator 2a emits pulse excitation light, the lens 2b focuses the pulse excitation light onto a specimen 5, and the lens 2c guides fluorescence photons emitted from the specimen 5 to the PMT 2d.

The controller 1 outputs a laser control signal S to the optical system 2. The laser control signal S input to the optical system 2 causes the laser oscillator 2a to emit pulse excitation light. The pulse excitation light is focused onto the specimen 5 through the lens 2b, and excites the specimen 5. Fluorescence photons are emitted from the excited specimen 5 and condensed to the PMT 2d through the lens 2c. The PMT 2d converts the fluorescence photons incident thereon into an electric signal E, and outputs the electric signal E to the measurer 3. The measurer 3 controls the respective gate lengths in response to gate control signals S1 and S2 received from the controller 1, and measures the numbers of fluorescence photons in the respective gate lengths. The measurer 3 outputs to a processor 4 measured-value signals Ct1 and Ct2 corresponding to the numbers of fluorescence photons measured in the respective gate lengths. The processor 4 calculates a fluorescence lifetime τ based on the measured-value signals Ct1 and Ct2, and outputs a signal indicating the fluorescence lifetime τ to the controller 1.

Figure 2:
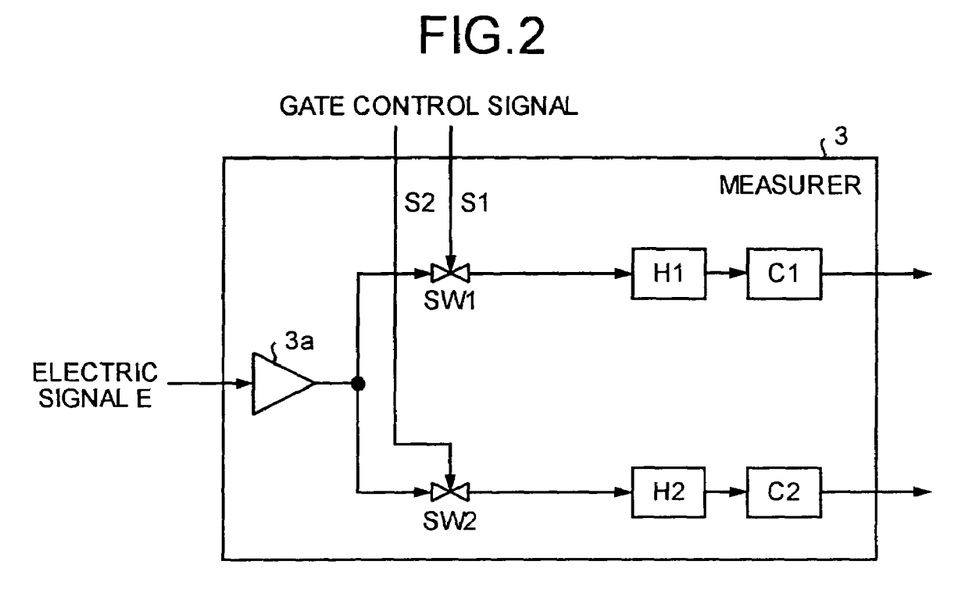
FIG. 2 is a block diagram of a measurer of the fluorescence lifetime measurement apparatus according to the first embodiment.

FIG. 2 is a block diagram of the measurer 3. The measurer 3 includes an amplifier 3a, switches SW1 and SW2, pulse height discriminators H1 and H2, and digital counters C1 and C2. The amplifier 3a amplifies the electric signal E input from the PMT 2d. The amplified electric signal E is transmitted to the switches SW1 and SW2. The switches SW1 and SW2 are controlled by gate control signals S1 and S2. When the gate control signals S1 and S2 are in an "ON" state, the switches SW1 and SW2 are closed, and the amplified electric signal E is transmitted to the pulse height discriminators H1 and H2. The pulse height discriminators H1 and H2 converts with a predetermined value the input signal into a binarized signal represented by "0" and "1", and output the binarized signal to the counters C1 and C2 respectively. The counters C1 and C2 count the number of signals "1" input thereto and outputs to the processor 4 measured-value signals Ct1 and Ct2 which indicate the numbers of fluorescence photons.

Figure 3:
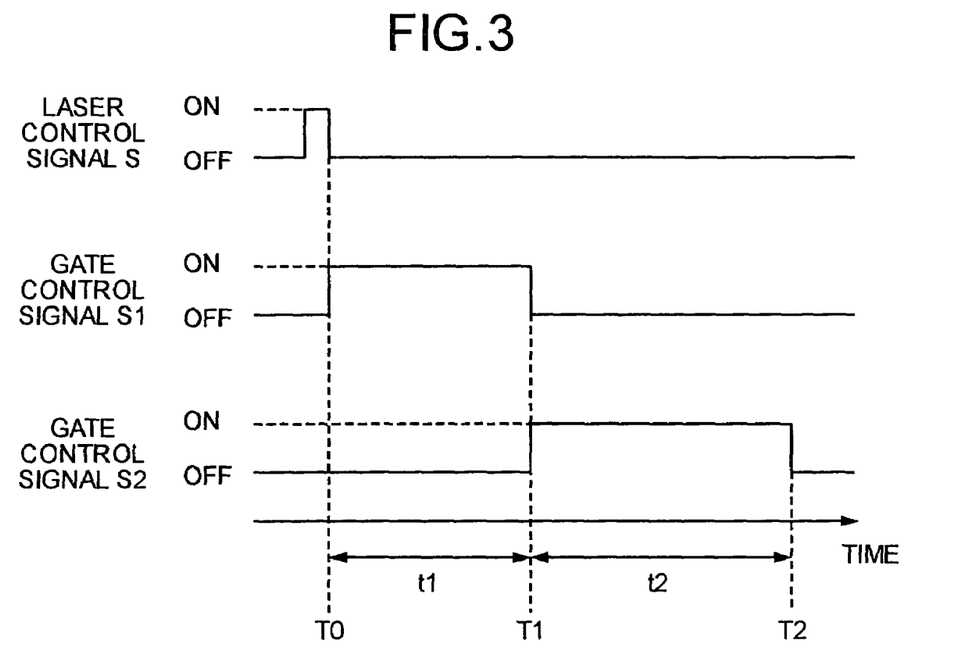
FIG. 3 is a time chart of a laser control signal S and gate control signals S1 and S2 which are used in the fluorescence lifetime measurement apparatus according to the first embodiment.

FIG. 3 shows a time chart of the laser control signal S and the gate control signals S1 and S2. Let T0 be a time at which the laser control signal S changes from "ON" to "OFF". As shown in FIG. 3, the gate control signal S1 is in an "ON" state during a period of time t1 (time T0 to T1), and the gate control signal S2 is in an "ON" state during a period of time t2 (time T1 to T2). This means that a first gate length is t1, a second gate length is t2, and a total gate length is (t1+t2). Here, let the first gate length t1 be a gate delay time t1.

Figure 4:
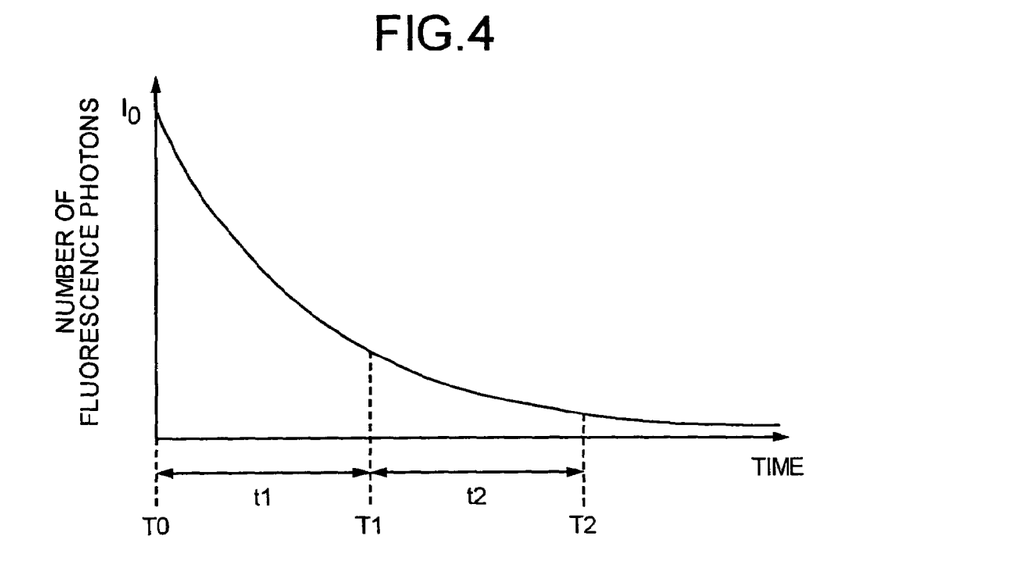
FIG. 4 is a graph indicating an attenuation characteristic of the number of fluorescence photons in the first embodiment.

Since an emission probability of the fluorescence photons emitted from the specimen 5 follows Poisson distribution, the number of fluorescence photons attenuates based on characteristics of natural logarithm during emission of the fluorescence photons. FIG. 4 is a characteristic graph which indicates that the number of fluorescence photons attenuates based on a predetermined attenuation constant.

The fluorescence lifetime τ is defined as a reciprocal of the attenuation constant of the number of fluorescence photons. Accordingly, the number of fluorescence photons I is given as a function of a period of time t by the following equation (1):

$$I = I_0 \exp\left(-\frac{t}{\tau}\right) \quad (1)$$

where $I_0$ is the number of fluorescence photons at time T0.

Let $I_1$ be the number of fluorescence photons measured during the first gate length t1, and let $I_2$ be the number of fluorescence photons measured during the second gate length t2. A ratio $I_2/I_1$ of $I_2$ to $I_1$ is represented by the following equation (2):

$$\frac{I_2}{I_1} = \frac{\int_{T1}^{T2} \exp\left(-\frac{t}{\tau}\right) dt}{\int_{T0}^{T1} \exp\left(-\frac{t}{\tau}\right) dt} \quad (2)$$

Let a ratio R be the ratio of $I_1$ and $I_2$ as shown by the following equation (3):

$$R = I_2/I_1 \quad (3)$$

If the ratio R is substituted for equation (2), the fluorescence lifetime τ is approximated by the following equation (4):

$$\tau = \frac{t1}{\ln + \dfrac{1+R}{R}} \quad (4)$$

where T2 is sufficiently large.

Accordingly, the processor 4 calculates the fluorescence lifetime X by calculating equation (4) based on the gate delay time t1 set by the controller 1 and the number of fluorescence photons $I_1$ and $I_2$ measured by the measurer 3, and outputs a signal indicating the fluorescence lifetime τ to the controller 1.

The controller 1 determines whether the fluorescence lifetime τ received from the processor 4 is within an appropriate error range, based on the gate delay time t1 and the total gate length (t1+t2). If the fluorescence lifetime τ is not within the appropriate error range, the controller 1 sets the gate delay time t1 and the total gate length (t1+t2) again, and recalculates the fluorescence lifetime τ.

Figure 5:
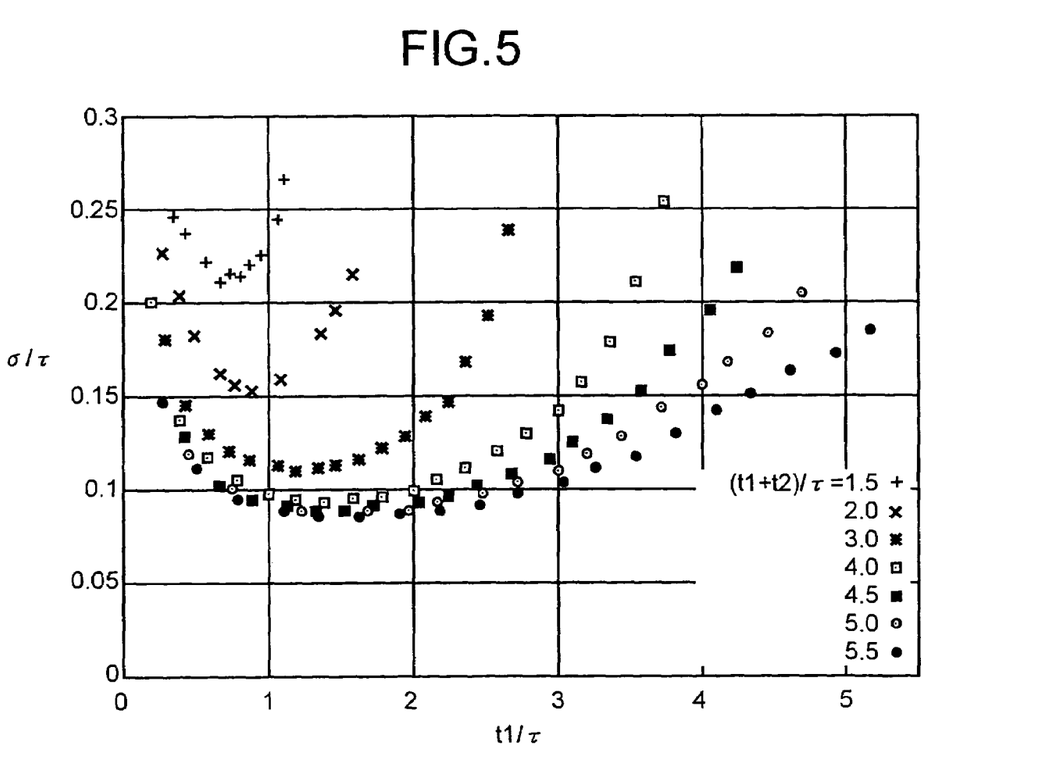
FIG. 5 is a graph indicating a characteristic of a standard deviation of a gate delay time normalized.

Determination criteria by the controller 1 is explained below. FIG. 5 is a characteristic graph indicating a standard deviation σ/τ with respect to the gate delay time t1 normalized by the fluorescence lifetime τ. A characteristic for each total gate length (t1+t2)/τ is shown in FIG. 5. Note that the characteristic is a result of calculation of the fluorescence lifetime τ repeated 5000 times by a Monte Carlo method with 250 photons. An error a is defined by the following equation (5):

$$\sigma = \sqrt{\frac{\sum_{i=1}^{k}(\tau_i - \tau)^2}{(k-1)}} \quad (5)$$

If the standard deviation σ/τ is used as indication of the error σ, a fluorescence lifetime τ satisfying a standard deviation σ/τ of 0.1 or less is generally acknowledged as high accuracy. As shown in FIG. 5, If the standard deviation σ/τ is 0.1 or less, a normalized gate delay time t1/τ satisfies $1 \leq t1/\tau \leq 2$, and a normalized total gate length (t1+t2)/τ satisfies $4 \leq (t1+t2)/\tau$. Thus, the controller 1 uses as decision criteria the following conditional inequalities (6) and (7):

$$((t1+t2)/\tau) \geq 4 \quad (6)$$

$$1 \leq t1/\tau \leq 2 \quad (7)$$

Figure 6:
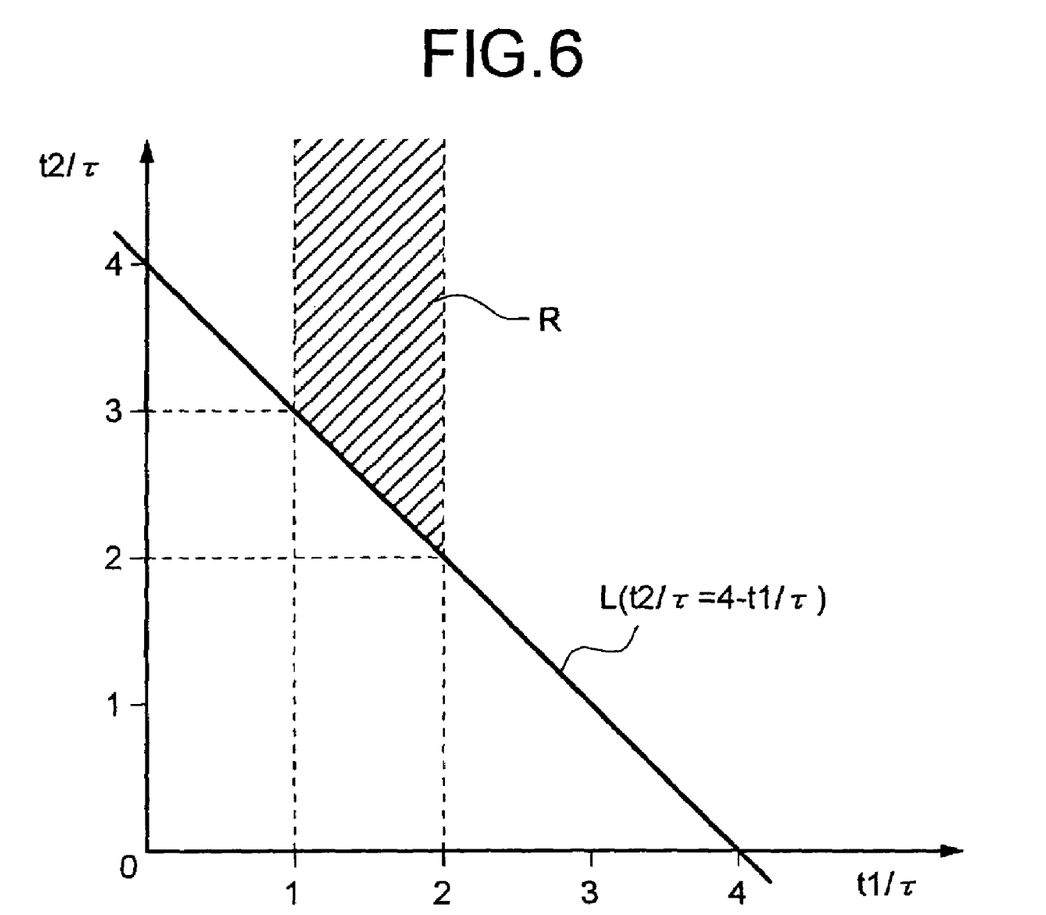
FIG. 6 is a graph indicating a region R satisfying $((t1+t2)/\tau) \geq 4$ and $1 \leq t1/\tau \leq 2$.

FIG. 6 shows a region R satisfying conditional inequalities (6) and (7). As shown in FIG. 6, t2/τ is expressed by a function L (t2/τ=4−t1/τ) of t1/τ. Further, the region R satisfying the two conditional inequalities ($1 \leq t1/\tau \leq 2$ and $4 \leq (t1+t2)/\tau$) is indicated by a shaded area in FIG. 6.

Accordingly, if t2/τ and t1/τ are within the region R, the determination unit 1c determines the fluorescence lifetime τ and finishes the calculation. If t2/τ and t1/τ are not within the region R, the determination unit 1c sets the gate delay time t1 and the total gate length (t1+t2) again.

Figure 7:
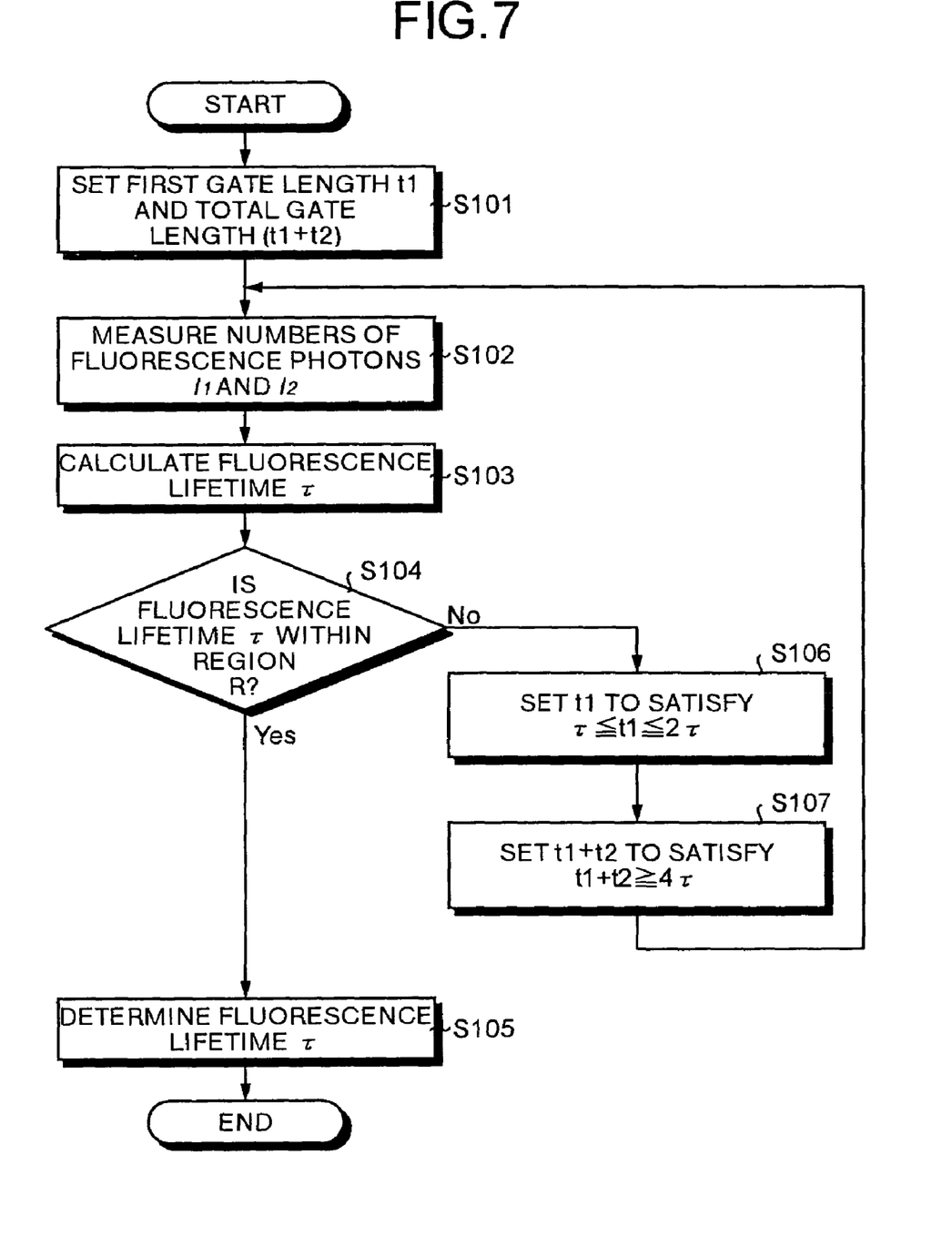
FIG. 7 is a flowchart of an operation of the fluorescence lifetime measurement apparatus according to the first embodiment until a fluorescence lifetime $\tau$ is determined.

FIG. 7 is a flowchart which depicts an operation of the fluorescence lifetime measurement apparatus 100 until the fluorescence lifetime τ is determined. The gate length control unit 1b sets the gate delay time t1, and the total gate length control unit 1a sets the total gate length (t1+t2) (step S101). The controller 1 outputs the laser control signal S to the optical system 2 as well as outputs the control signals S1 and S2 to the measurer 3, and measures the number of fluorescence photons $I_1$ and $I_2$ (step S102). The measurer 3 outputs the measured-value signals Ct1 and Ct2 corresponding to the number of measured fluorescence photons, to the processor 4. The processor 4 calculates the fluorescence lifetime τ based on the measured-value signals Ct1 and Ct2 (step S103). The fluorescence lifetime τ calculated is transmitted to the determination unit 1c. The determination unit 1c determines whether the input fluorescence lifetime τ is within the region R (step S104). If the fluorescence lifetime τ is within the region R (step S104, YES), the determination unit 1c determines the fluorescence lifetime τ (step S105). If the fluorescence lifetime τ is not within the region R (step S104, NO), the gate length control unit 1b sets the gate delay time t1 which satisfies $\tau \leq t1 \leq 2\tau$ (step S106). The total gate length control unit 1a sets the total gate length (t1+t2) which satisfies $t1+t2 \geq 4\tau$, based on the gate delay time t1 (step S107). Note that, set of the gate delay time t1 (step S106) and set of the total gate length (t1+t2) (step S107) may be executed at the same time.

Figure 8:
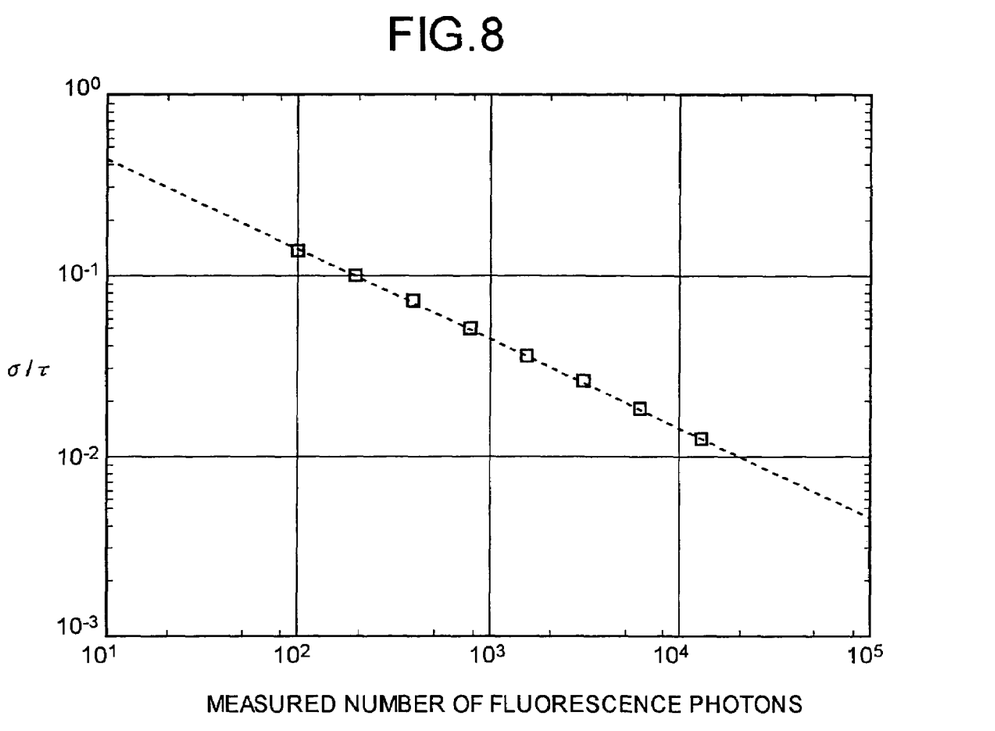
FIG. 8 is a graph indicating a relation of the standard deviation and the number of fluorescence photons measured by the measurer.

FIG. 8 is a characteristic graph indicating a relation of the standard deviation σ/τ and the number of fluorescence photons measured by the measurer 3. As shown in FIG. 8, the standard deviation σ/τ is 0.1 or less for 185 fluorescence photons. Conventionally, 250 or more of fluorescence photons are required for a standard deviation σ/τ of 0.1 or less. Accordingly, the fluorescence lifetime τ with approximately the same level of error can be calculated using about three fourth of the conventional number of measured fluorescence photons or less.

In the first embodiment, whether the t1/τ and t2/τ are within the region R is determined after the fluorescence lifetime τ is calculated, and thus either the fluorescence lifetime τ is determined or the gate delay time t1 and the total gate length (t1+t2) are set again. As a result, the fluorescence lifetime τ of high accuracy can be calculated in a short time.

Figure 9:
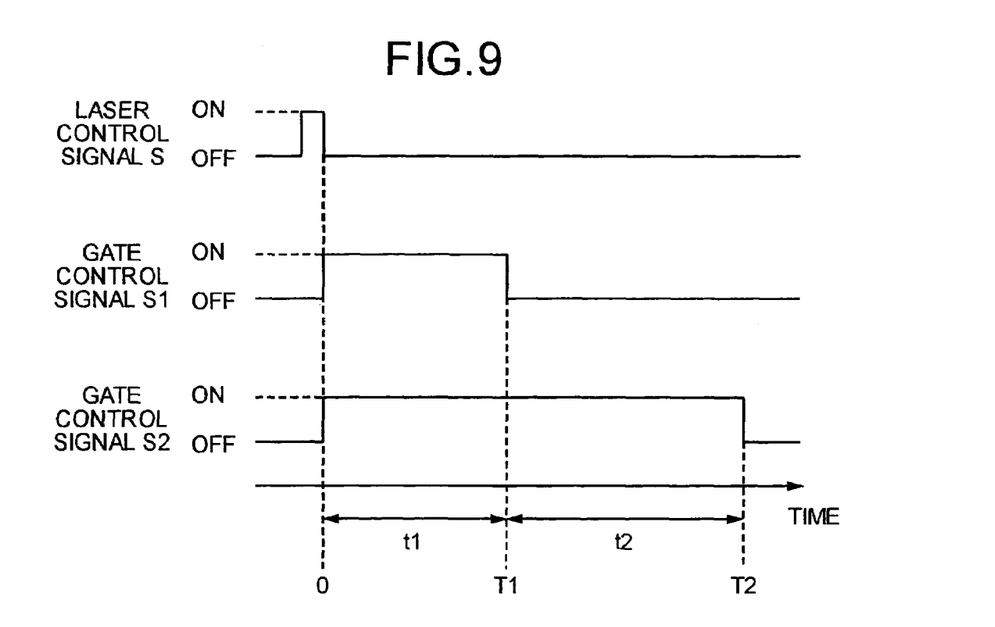
FIG. 9 is another time chart of the laser control signal S and the gate control signals S1 and S2.

Note that, in the first embodiment, the gate control signals S1 and S2 of the measurer 3 individually control the gate delay time t1 and the second gate length t2. As shown in a time chart of FIG. 9, the gate delay time t1 may be controlled based on the gate control signal S1, and the total gate length (t1+t2) may be controlled based on the gate control signal S2.

Figure 10:
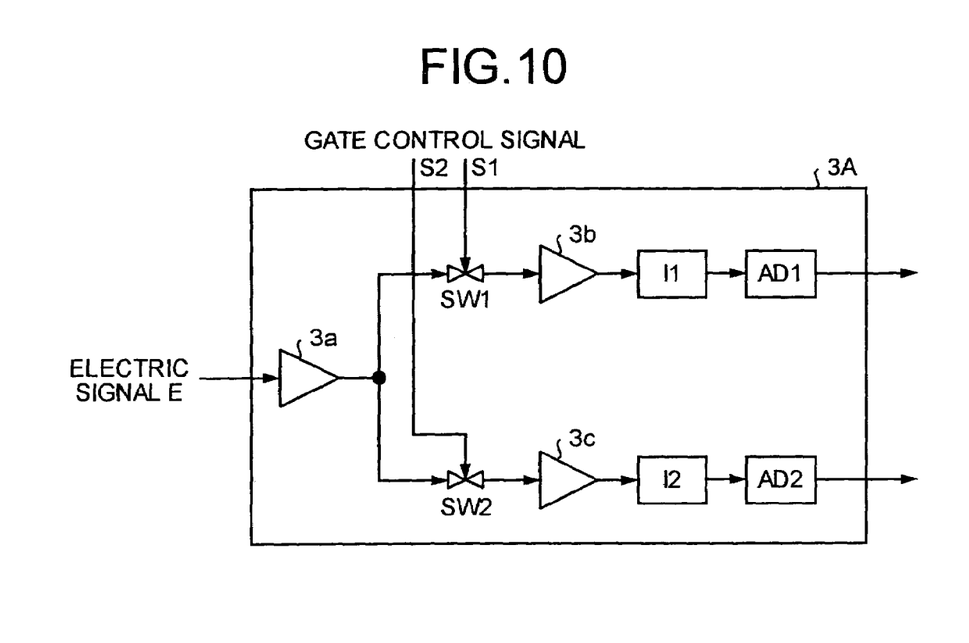
FIG. 10 is a block diagram of another measurer of the fluorescence lifetime measurement apparatus according to the first embodiment.

A measurer 3A shown in FIG. 10 in place of the measurer 3 may be used if the specimen 5 has a high emission probability of fluorescence photons. The measurer 3A includes amplifiers 3a, 3b, and 3c, switches SW1 and SW2, integrators 11 and 12, and A/D converters AD1 and AD2. The electric signal E input to the measurer 3A is transmitted to the integrators 11 and 12 through the amplifier 3a, the switches SW1 and SW2, and further the amplifiers 3b and 3c. The electric signal E is integrated by the integrators 11 and 12, and sampled and converted into digital signals by the A/D converters AD1 and AD2. The measurer 3A uses the digital signals output from the A/D converters AD1 and AD2 as the measured-value signals Ct1 and Ct2 indicating the number of fluorescence photons Thus, even if the specimen 5 has a high emission probability of fluorescence photons and the electric signal E is not formed in a pulse shape, the number of fluorescence photons can be accurately measured because the A/D converters AD1 and AD2 make sampling in correspondence to one photon.

Figure 11:
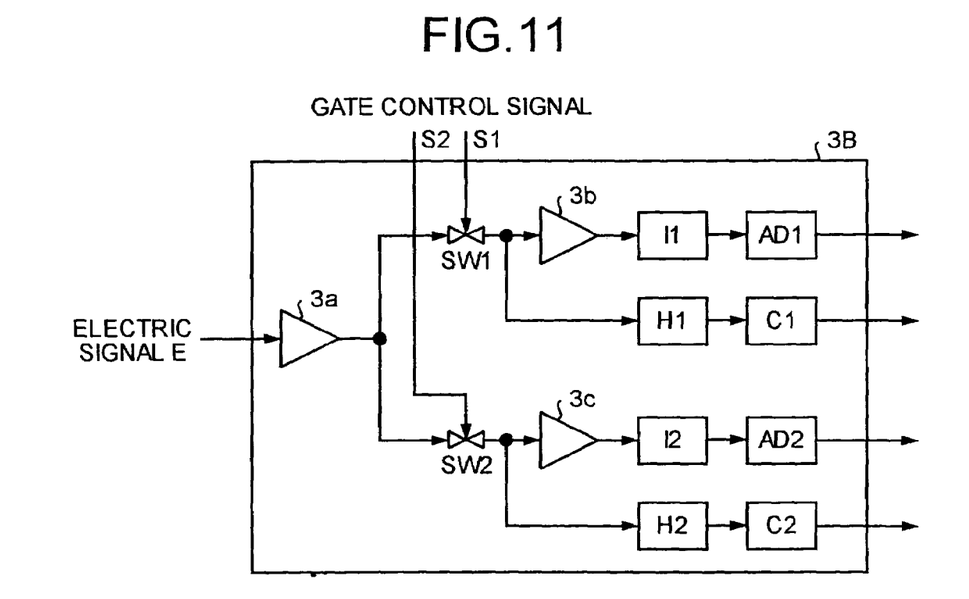
FIG. 11 is a block diagram of still another measurer of the fluorescence lifetime measurement apparatus according to the first embodiment.

A measurer 3B shown in FIG. 11 in place of the measurer 3 may be used. The measurer 3B can measure the number of fluorescence photons, regardless of an emission probability of fluorescence photons of the specimen 5. The measurer 3B shown in FIG. 11 is arranged by combining the configuration of the measurer 3 shown in FIG. 2 with that of the measurer 3A shown in FIG. 10. Thus, the processor 4 can select the measured-value signals Ct1 and Ct2 of the number of fluorescence photons based on a emission ratio of fluorescence photons emitted from the specimen 5. Further, the processor 4 can calculate two kinds of fluorescence lifetime τ, and select and output a more appropriate fluorescence lifetime τ.

Figure 12:
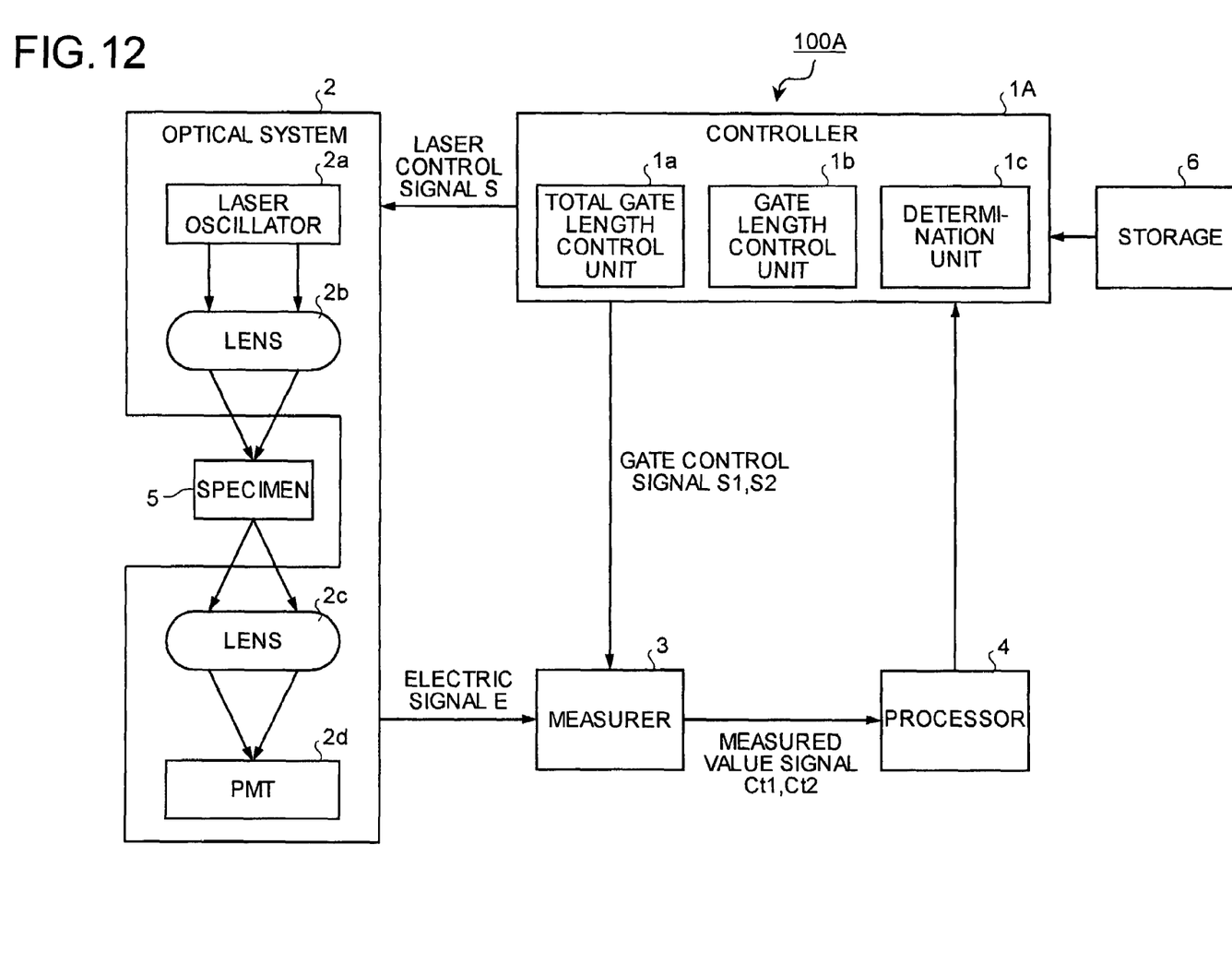
FIG. 12 is a block diagram of a fluorescence lifetime measurement apparatus being a modification of the first embodiment.

FIG. 12 is a block diagram of a fluorescence lifetime measurement apparatus 100A being a modification of the first embodiment. As shown in FIG. 12, the fluorescence lifetime measurement apparatus 100A includes a storage 6 connected to a controller 1A. The storage 6 stores the characteristic graph shown in FIG. 5 as a table. When the processor 4 outputs a signal indicating the fluorescence lifetime τ, appropriate t1/τ and appropriate (t1+t2)/τ are input from the table stored in the storage 6 to the controller 1A, which determines whether the input fluorescence lifetime τ is appropriate. Thus, a time for calculating t1/τ and (t1+t2)/τ can be saved, thereby the fluorescence lifetime τ of high accuracy can be determined in a shorter time.

A second embodiment is explained below. In the first embodiment, the number of fluorescence photons is measured just after the specimen 5 is irradiated with the pulse excitation light. In the second embodiment, however, a delay time is set before measurement of the number of fluorescence photons starts so that the number can be calculated accurately.

Figure 13:
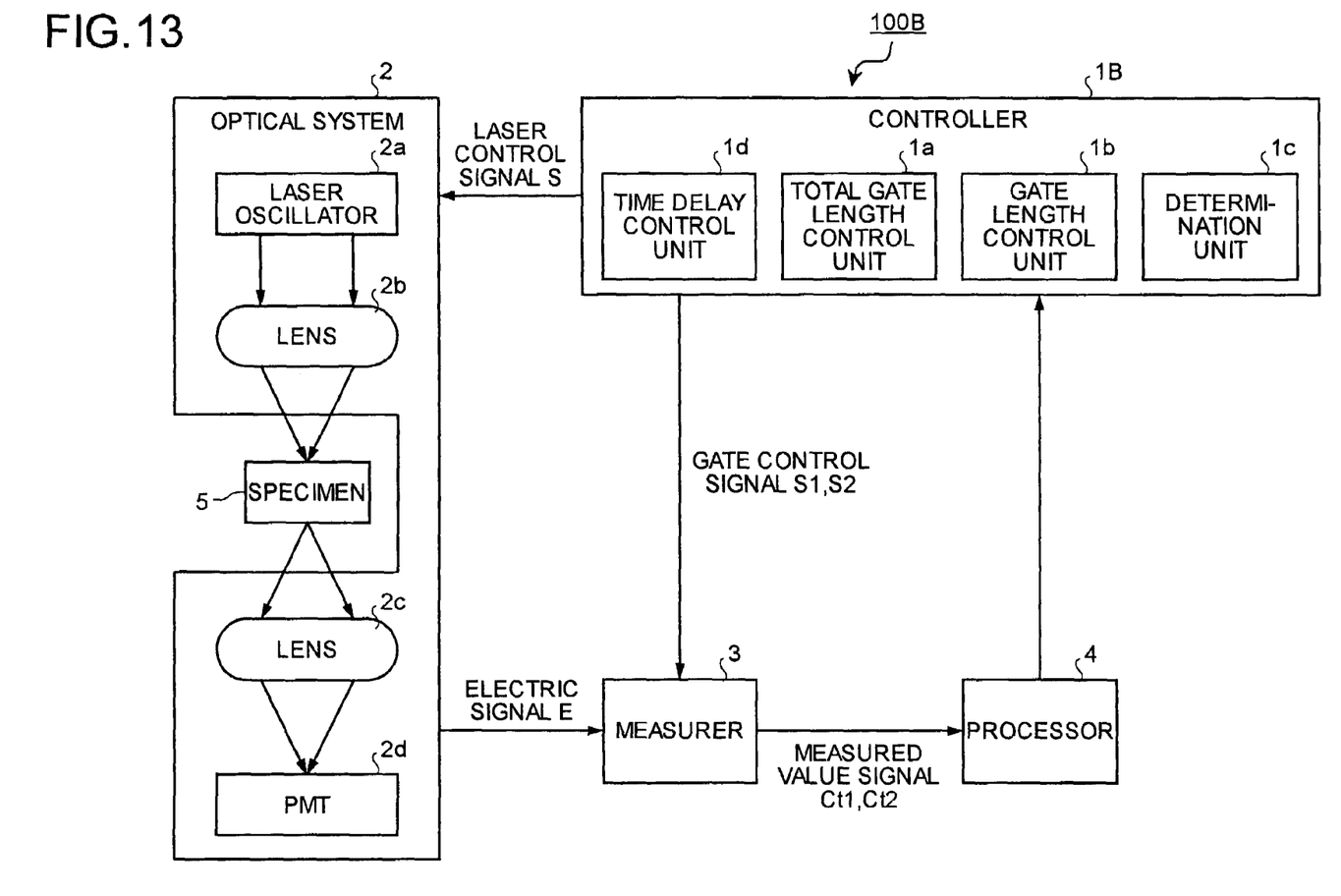
FIG. 13 is a block diagram of a fluorescence lifetime measurement apparatus according to a second embodiment of the present invention.

FIG. 13 is a block diagram a fluorescence lifetime measurement apparatus 100B according to the second embodiment of the present invention. As shown in FIG. 13, a controller 1B includes a time delay control unit 1d. The time delay control unit 1d sets gate control signals S1 and S2 such that measurement of fluorescence photons is delayed until emission of fluorescence photons becomes equal to or less than a light sensitivity of the PMT 2d.

Since an emission probability of fluorescence photons emitted from an excited specimen follows Poisson distribution, the number of fluorescence photons is maximized just after emission of the excitation light, and thus may exceed the light sensitivity of the PMT 2d. In this case, the number of fluorescence photons cannot be correctly measured, and thus a calculated fluorescence lifetime τ has a large error a. Thus, the time delay control unit 1d sets an appropriate delay time so that the number of fluorescence photons can be accurately calculated.

Figure 14:
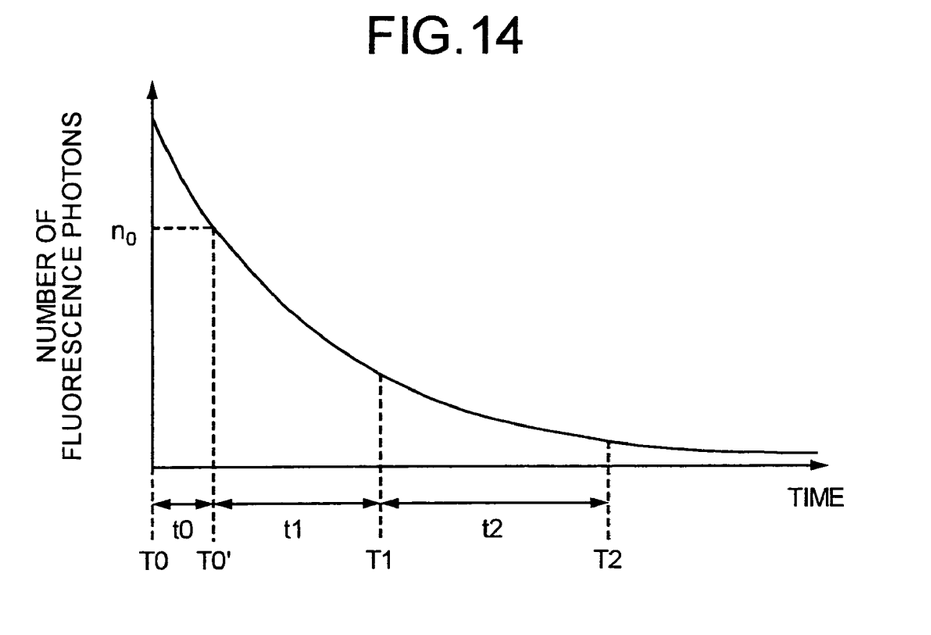
FIG. 14 is a graph indicating an attenuation characteristic of the number of fluorescence photons in the second embodiment.
Figure 15:
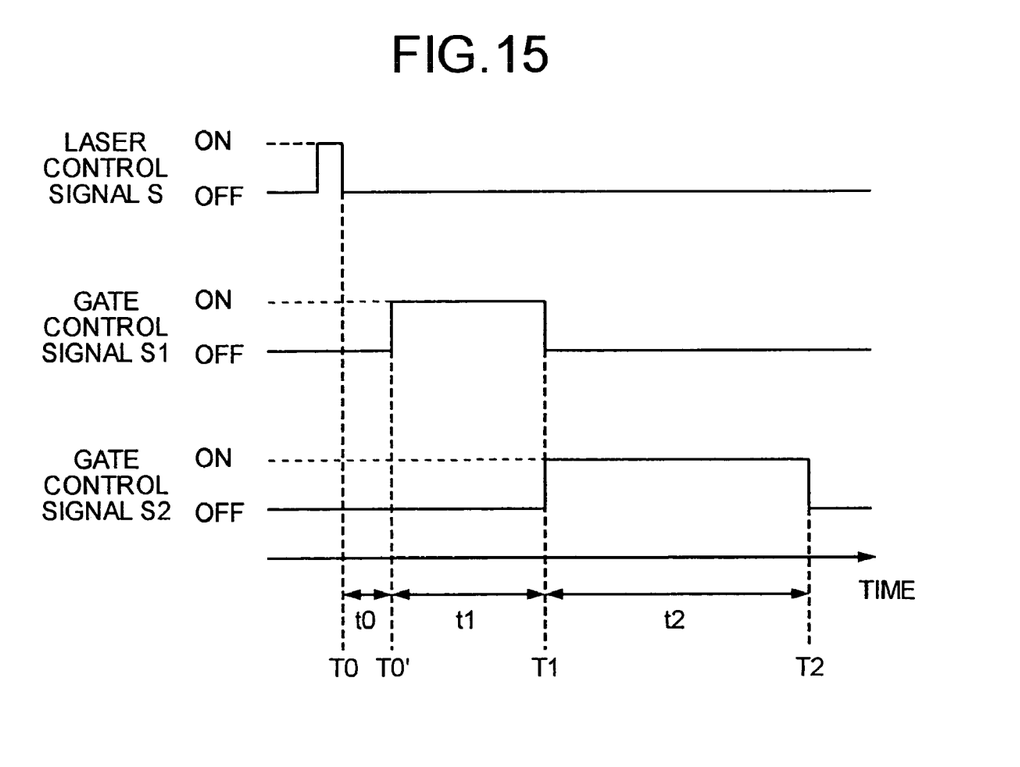
FIG. 15 is a time chart of a laser control signal S and gate control signals S1 and S2 which are used in the fluorescence lifetime measurement apparatus according to the second embodiment.

FIG. 14 is an attenuation characteristic graph indicating that a limit of the light sensitivity of the PTM 2d corresponds to the number of fluorescence photons no. Accordingly, the time delay control unit 1d sets a delay time t0 (time T0 to T0') so that the number of fluorescence photons is measured after it attenuates to no. FIG. 15 shows a time chart of a laser control signal S and gate control signals S1 and S2.

As shown in FIG. 15, a gate delay time t1 is set from a time T0' to a time T1, a second gate length t2 is set from the time T1 to a time T2, and a total gate length (t1+t2) is set from the time T0' to the time T2. Accordingly, if the number of fluorescence photons measured during the gate delay time t1 is shown by $I_1$ and the number of fluorescence photons measured during the second gate length t2 is shown by $I_2$, a ratio $I_2/I_1$ of $I_2$ to $I_1$ is expressed by the following equation (2)':

$$\frac{I_2}{I_1} = \frac{\int_{T1}^{T2} \exp\left(-\frac{t}{\tau}\right) dt}{\int_{T0'}^{T1} \exp\left(-\frac{t}{\tau}\right) dt} \quad (2)'$$

Accordingly, the fluorescence lifetime τ can be calculated by the equation (2)' in place of equation (2) explained in the first embodiment.

In the second embodiment, provision of the delay time after fluorescence photons are emitted enables the number of fluorescence photons to be measured accurately and the fluorescence lifetime τ to converge in a short time. Note that, in the second embodiment, the delay time is set based on the lightsensitivity of the PMT 2d. However, it may be set in conformity with an emission probability of fluorescence photons discharged from the specimen 5 and with resolution of the apparatus in its entirety to the number of fluorescence photons.

A third embodiment is explained below. In the first and second embodiments, the processor 4 calculates and outputs the fluorescence lifetime τ, and the determination unit 1c determines whether the gate delay time t1 and the total gate length (t1+t2) are appropriate based on the fluorescence lifetime τ. In the third embodiment, however, a first gate length and a second gate length are set to the same time length, and a time difference between a time at which the first gate length starts and a time at which the second gate length starts is set as a gate delay time. Whether the gate delay time t1 and the total gate length (t1+t2) are appropriate depends on measured value signals Ct1 and Ct2 output from the measurer 3 so that unnecessary calculation of the fluorescence lifetime τ can be omitted.

Figure 16:
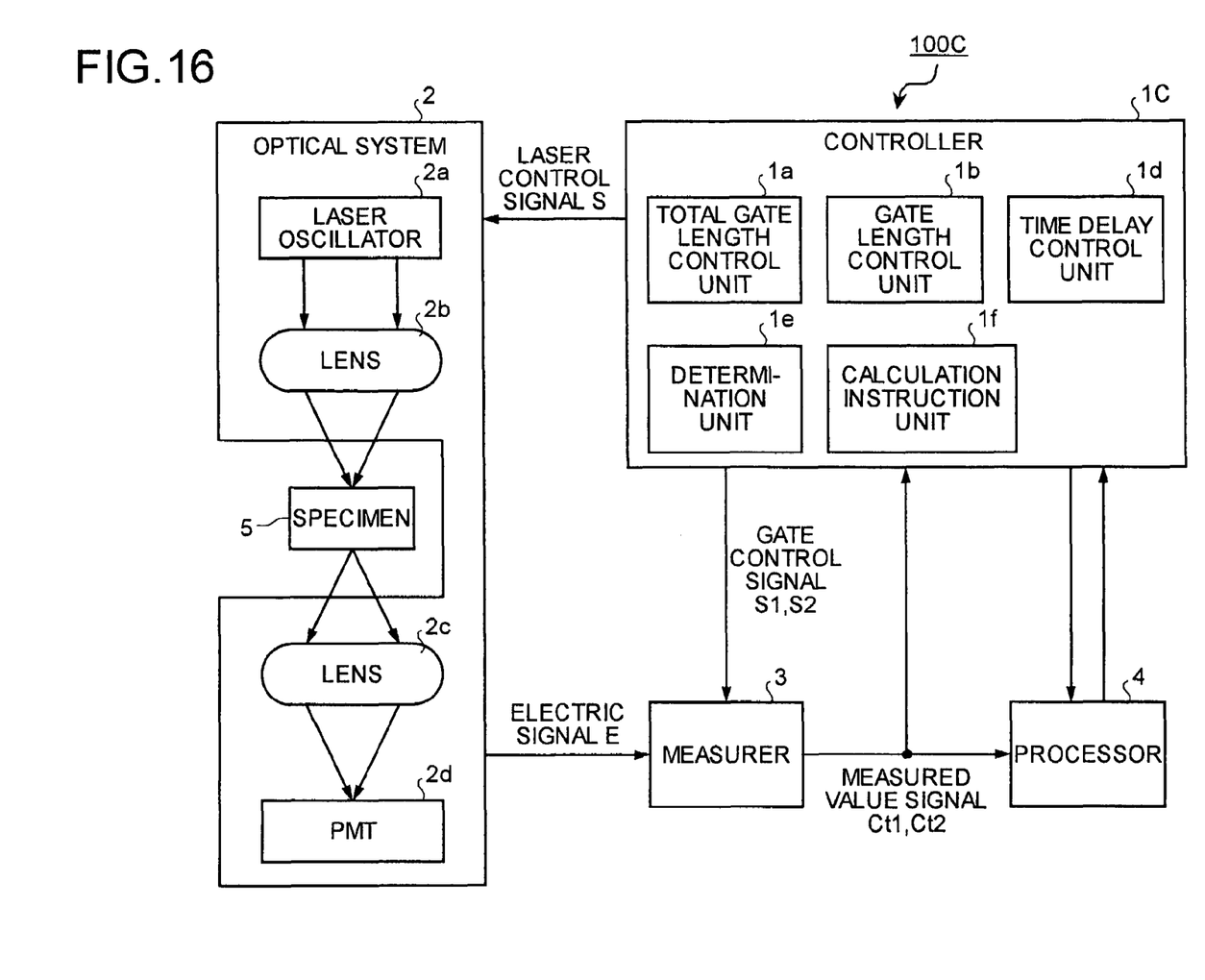
FIG. 16 is a block diagram of a fluorescence lifetime measurement apparatus according to a third embodiment of the present invention.

FIG. 16 is a block diagram of a fluorescence lifetime measurement apparatus 100C according to the third embodiment. As shown in FIG. 16, the measurer 3 measures the number of fluorescence photons 1i and 12 by inputting an electric signal E and outputs measured-value signals Ct1 and Ct2 to a controller 1C and the processor 4. The controller 1C determines whether a gate delay time t1 and a total gate length (t1+t2) are appropriate based on the measured-value signals Ct1 and Ct2 input thereto. When the gate delay time t1 and the total gate length (t1+t2) are not appropriate, the digital counter C1 set them again, and as long as they are appropriate, the controller 1C calculates a fluorescence lifetime τ through the processor 4.

Figure 17:
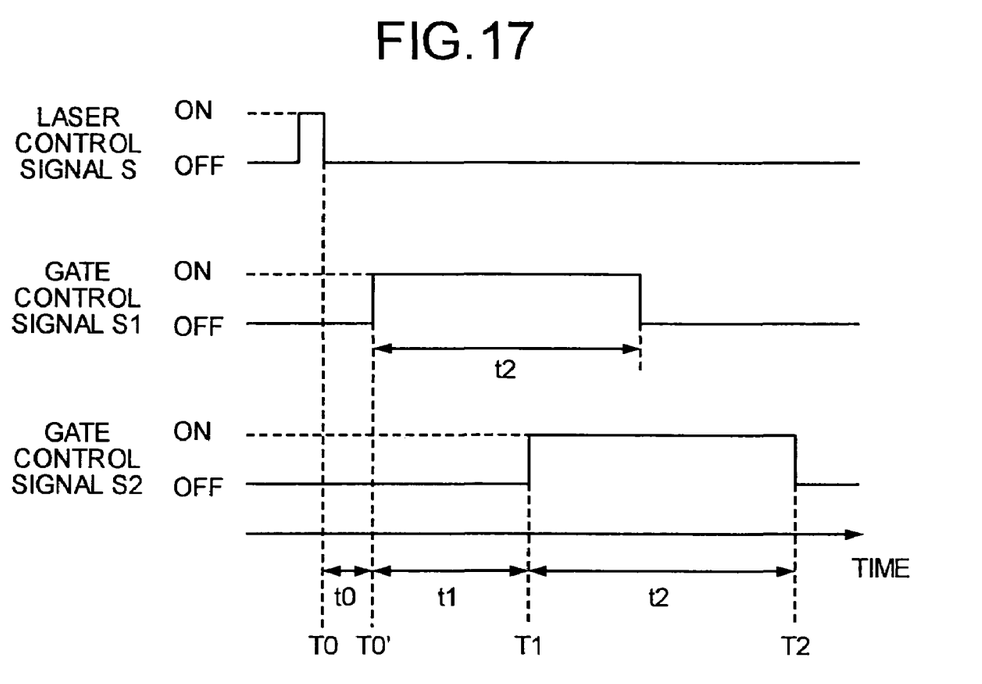
FIG. 17 is a time chart of a laser control signal S and gate control signals S1 and S2 which are used in the fluorescence lifetime measurement apparatus according to the third embodiment.

FIG. 17 shows a time chart of a laser control signal S and gate control signals S1 and S2. As shown in FIG. 17, "ON" period of times of the gate control signals S1, S2 are set to the same period of time t2, and a time difference between the time at which the first gate length t2 starts and the time at which the, second gate length starts is set as a gate delay time t1. Accordingly, a total gate length is expressed by (t1+t2).

When the first gate length t2 and the second gate length t2 have the same gate length t2 and the numbers of fluorescence photons measured by the respective gate lengths are expressed by $I_1$ and $I_2$, the fluorescence lifetime τ is expressed by the following equation (4)':

$$\tau = \frac{t1}{\ln\frac{I_1}{I_2}} \quad (4)'$$

The total gate length (t1+t2) is expressed by the following inequality (6)' which is a modification of inequality (6) explained in the first embodiment:

$$t1+t2 \geq 4\tau \quad (6)'$$

On the other hand, a ratio $(I_1/I_2)$ between the numbers of fluorescence photons $I_1$ and $I_2$ is expressed by the following inequality (7)' which is a modification of inequality (7) explained in the first embodiment likewise:

$$e \leq I_1/I_2 \leq e^2 \quad (7)'$$

When an approximate value (e≈2.72) is substituted for a base "e" of natural logarithm shown in the inequality (7)', inequality (7)' is approximated by the following inequality (7)":

$$2.72 \leq (I_1/I_2) \leq e^2 \quad (7)''$$

Accordingly, a determination unit 1e determines whether the ratio ($I_1/I_2$) between the numbers of fluorescence photons $I_1$ and $I_2$ satisfies inequality (7)" from the measured-value signals Ct1 and Ct2 corresponding to the number of fluorescence photons $I_1$ and $I_2$. When the ratio ($I_1/I_2$) between the numbers of fluorescence photons $I_1$ and $I_2$ satisfies inequality (7)", a calculation instruction unit 1f causes the processor 4 to calculate the fluorescence lifetime τ. When the ratio ($I_1/I_2$) between the numbers of fluorescence photons $I_1$ and $I_2$ does not satisfy inequality (7)", the determination unit 1e sets the first gate length t2 and the total gate length (t1+t2) again.

Figure 18:
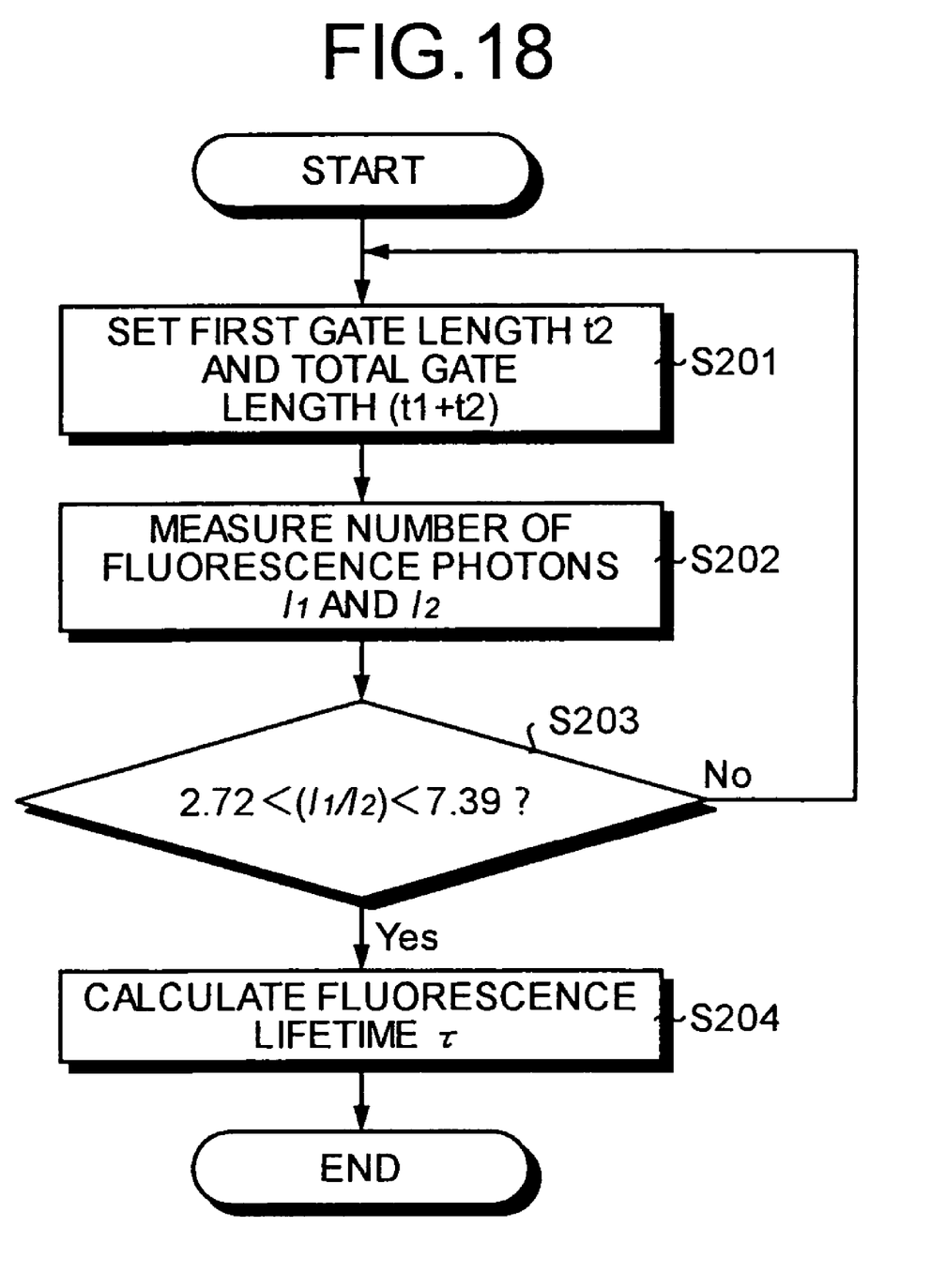
FIG. 18 is a flowchart of an operation of the fluorescence lifetime measurement apparatus according to the third embodiment until a fluorescence lifetime τ is determined.

FIG. 18 is a flowchart of an operation of the fluorescence lifetime measurement apparatus 100C until the fluorescence lifetime τ is settled. The gate length control unit 1b sets the first gate length t2, the total gate length control unit 1a sets the total gate length (t1+t2) (step S201). Next, the measurer 3 measures the numbers of fluorescence photons $I_1$ and $I_2$ (step S202). The measurer 3 outputs the measured-value signals Ct1 and Ct2 corresponding to the numbers of fluorescence photons $I_1$ and $I_2$ to the controller 1C. A determination unit 1e in the controller 1C determines whether the ratio ($I_1/I_2$) between the numbers of fluorescence photons $I_1$ and $I_2$ satisfies $2.72 \leq I_1/I_2 \leq 7.39$ based on the measured-value signals Ct1 and Ct2 (step S203). When the ratio ($I_1/I_2$) satisfies $2.72 \leq I_1/I_2 \leq 7.39$ (step S203, YES), the calculation instruction unit if causes the processor 4 to calculate the fluorescence lifetime τ (step S204). When the ratio ($I_1/I_2$) does not satisfy $2.72 \leq I_1/I_2 \leq 7.39$ (step S203, NO), the determination unit 1e sets the first gate length t2 and the total gate length (t1+t2) again.

When the first gate length t2 and the total gate length (t1+t2) are set again, the first gate length t2 may be set appropriately and only the gate delay period of time t1 may be changed based on inequality (7)' without changing the first gate length t2 and the second gate length t2. In this case, since portions to be changed are small in number, the first gate length t2 and the total gate length (t1+t2) can be set appropriately in a shorter time.

In the third embodiment, whether the first gate length t2 and the total gate length (t1+t2) are appropriate can be easily determined by setting the first gate length t2 and the second gate length t2 to the same length and determining whether the ratio ($I_1/I_2$) between the numbers of fluorescence photons $I_1$ and $I_2$, which are measured by the first gate length t2 and the second gate length t2, satisfies a conditional equation employing specific values. Accordingly, when the fluorescence lifetime τ is calculated only when the first gate length t2 and the total gate length (t1+t2) are determined appropriate, the fluorescence lifetime τ of high accuracy can be settled at a high speed by omitting unnecessary calculation of the fluorescence lifetime τ.

Note that, in the first to three embodiments although a plurality of gate lengths are set as the two gate lengths, that is the first and second gate lengths t1 and t2, they may be set as three or more gate lengths.

Thus, the fluorescence lifetime of high accuracy can be calculated in a short time by a simple method.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A fluorescence lifetime measurement apparatus comprising:
   a light source irradiating a specimen with excitation light;
   a first controller controlling a total gate length that is a total time window during which a number of fluorescence photons emitted from the specimen excited by the excitation light is measured;
   a second controller controlling a start gate length of a plurality of gate lengths into which the total gate length is divided, the start gate length being a time window whose start time is when measurement of the number of fluorescence photons starts;
   a measurer measuring the number of fluorescence photons for each of the gate lengths;
   a processor calculating a fluorescence lifetime the specimen based on the start gate length and the number of fluorescence photons measured by the measurer; and
   a third controller causing, when the fluorescence lifetime does not satisfy a predetermined condition, the first controller and the second controller to change the start gate length and the total gate length.

2. The fluorescence lifetime measurement apparatus according to claim 1, wherein the predetermined condition is an expression showing a relation among the fluorescence lifetime, the start gate length, and the total gate length.

3. The fluorescence lifetime measurement apparatus according to claim 2, wherein the expression is $1 \leq (t1/\tau) \leq 2$ and $(t1+t2)/\tau \geq 4$, where τ is the fluorescence lifetime, t1 is the start gate length, and t1+t2 is the total gate length.

4. The fluorescence lifetime measurement apparatus according to claim 3, further comprising a storage unit storing the start gate length normalized by the fluorescence lifetime and the total gate length by the fluorescence lifetime.

5. The fluorescence lifetime measurement apparatus according to claim 1, further comprising a time delay controller delaying a start of measurement of the number of fluorescence photons until the fluorescence photons become equal to or less than a predetermined number after the specimen is irradiated with the excitation light.

6. A fluorescence lifetime measurement apparatus comprising:
   a light source irradiating a specimen with excitation light;
   a first controller controlling a total gate length that is a total time window during which a number of fluorescence photons emitted from the specimen excited by the excitation light is measured;
   a second controller controlling a start gate length of a plurality of gate lengths obtained from the total gate length, the start gate length being a time window whose start time is when measurement of the number of fluorescence photons starts;
   a measurer measuring the number of fluorescence photons for each of the gate lengths;
   a processor calculating a fluorescence lifetime the specimen based on the start gate length and the number of fluorescence photons measured by the measurer; and
   a third controller causing, when a ratio in the number of fluorescence between the gate lengths does not satisfy a predetermined condition, the first controller and the second controller to change the start gate length and the total gate length.

7. The fluorescence lifetime measurement apparatus according to claim 6, wherein the predetermined condition is such that when a first gate length and a second gate length are set to the same time length, and when the first gate length starts to measure the number of fluorescence photons prior to the second gate length, the number of fluorescence photons measured during the first gate length is about 2.72 or more and about 7.93 or less with respect to the number of gate fluorescence photons measured during the second gate length.

8. The fluorescence lifetime measurement apparatus according to claim 7, further comprising a storage unit storing the predetermined condition as to the number of fluorescence photons measured during the first gate length with respect to the number of gate fluorescence photons measured during the second gate length.

9. The fluorescence lifetime measurement apparatus according to claim 7, wherein the first gate length and the second gate length have an overlapping time portion, and the start time length is a time difference between a start of the first gate length and a start of the second gate length.

10. The fluorescence lifetime measurement apparatus according to claim 9, further comprising a storage unit storing the predetermined condition as to the number of fluorescence photons measured during the first gate length with respect to the number of gate fluorescence photons measured during the second gate length.

11. The fluorescence lifetime measurement apparatus according to claim 6, further comprising a time delay controller delaying a start of measurement of the number of fluorescence photons until the fluorescence photons become equal to or less than a predetermined number after the specimen is irradiated with the excitation light.

* * * * *